(12) United States Patent
    Berens

(10) Patent No.: US 8,998,950 B2
(45) Date of Patent: Apr. 7, 2015

(54) SYSTEM AND METHOD FOR SEALING ACCESS

(76) Inventor: Eric Berens, Tucson, AZ (US)

( * ) Notice: Subject to any disclaimer, the term of this patent is extended or adjusted under 35 U.S.C. 154(b) by 518 days.

(21) Appl. No.: 13/405,911

(22) Filed: Feb. 27, 2012

(65) Prior Publication Data

US 2012/0221043 A1 Aug. 30, 2012

Related U.S. Application Data

(60) Provisional application No. 61/447,483, filed on Feb. 28, 2011.

(51) Int. Cl.
    *A61B 17/03* (2006.01)
    *A61B 17/00* (2006.01)
    *A61B 19/00* (2006.01)

(52) U.S. Cl.
    CPC ... *A61B 17/0057* (2013.01); *A61B 2017/00004* (2013.01); *A61B 2017/00367* (2013.01); *A61B 2017/00424* (2013.01); *A61B 2017/00623* (2013.01); *A61B 2017/00654* (2013.01); *A61B 2017/00672* (2013.01); *A61B 2019/444* (2013.01); *A61B 2019/462* (2013.01); *A61B 2019/4857* (2013.01)

(58) Field of Classification Search
    USPC .......................................... 606/213
    See application file for complete search history.

(56) References Cited

U.S. PATENT DOCUMENTS

| | | | |
|---|---|---|---|
| 6,033,427 A | 3/2000 | Lee | 606/213 |
| 6,719,781 B1 | 4/2004 | Kim | 623/1.13 |
| 6,790,220 B2 | 9/2004 | Morris et al. | 606/213 |
| 7,879,061 B2 | 2/2011 | Keith et al. | 606/199 |
| 2006/0004408 A1 | 1/2006 | Morris et al. | 606/215 |

OTHER PUBLICATIONS

PCT International Search Report and Written Opinion, dated Sep. 6, 2012 (11 pgs).

*Primary Examiner* — Ryan Severson
(74) *Attorney, Agent, or Firm* — Hayes Soloway P.C.

(57) ABSTRACT

The present invention relates to an apparatus and a method for sealing a puncture in a tubular tissue structure or the wall of a body cavity. More specifically, the present invention is directed to an apparatus and method for sealing a puncture site in the wall of a tubular tissue structure, or in the wall of a body cavity with a stabilizer used to stabilize the material used to seal the puncture site as the material is positioned. The material is inserted into the puncture site as a ribbon or sheet on an introducer element such as a needle, a cannula, a guide wire, an introducer element adapted for dialysis, an introducer element adapted for catheterization, a trocar, or any other introducer element used to access the lumen of a tubular tissue structure or used to access a body cavity.

19 Claims, 10 Drawing Sheets

SYSTEM AND METHOD FOR SEALING ACCESS

CROSS REFERENCE TO RELATED APPLICATION

This application claims priority from U.S. Provisional Application Ser. No. 61/447,483, filed Feb. 28, 2011, the contents of which are incorporated herein by reference.

BACKGROUND

1. Field

The present invention relates to an apparatus and a method for achieving rapid hemostasis in sealing a puncture in a tubular tissue structure or the wall of a body cavity. More particularly, the present invention is directed to sealing a puncture site with submucosal tissue or another extracellular matrix-derived tissue capable of remodeling endogenous connective tissue.

2. Description of Related Art

The control of bleeding during and after surgery is important to the success of the procedure. The control of blood loss is of particular concern if the surgical procedure is performed directly upon or involves the patient's arteries and veins. Well over one million surgical procedures are performed annually which involve the insertion and removal of catheters into and from arteries and veins. Accordingly, these types of vasculature procedures represent a significant amount of surgery in which the control of bleeding is of particular concern.

Typically, the insertion of a catheter creates a puncture through the vessel wall and upon removal the catheter leaves a puncture opening through which blood may escape and leak into the surrounding tissues. Therefore, unless the puncture site is closed clinical complications may result leading to increased hospital stays with the associated costs. To address this concern, medical personnel are required to provide constant and continuing care to a patient who has undergone a procedure involving an arterial or venous puncture to insure that post-operative bleeding is controlled.

Surgical bleeding concerns can be exacerbated by the administration of a blood thinning agent, such as heparin, to the patient prior to a catheterization procedure. Since the control of bleeding in anti-coagulated patients is much more difficult to control, stemming blood flow in these patients can be troublesome. A common method of healing the puncture to the vessel is to maintain external pressure over the vessel until the puncture seals by natural clot formation processes. This method of puncture closure typically takes about thirty to ninety minutes, with the length of time usually being greater if the patient is hypertensive or anti-coagulated.

Furthermore, it should be appreciated that utilizing pressure, such as human hand pressure, to control bleeding suffers from several drawbacks regardless of whether the patient is hypertensive or anti-coagulated. In particular, when human hand pressure is utilized, it can be uncomfortable for the patient, can result in excessive restriction or interruption of blood flow, and can use costly professional time on the part of the hospital staff. Other pressure techniques, such as pressure bandages, sandbags, or clamps require the patient to remain motionless for an extended period of time and the patient must be closely monitored to ensure the effectiveness of these techniques.

Other devices have been disclosed which plug or otherwise provide an obstruction in the area of the puncture. In current practice, submucosal tissue or another extracellular matrix-derived tissue is used to seal punctures in tubular tissue structures, such as blood vessels, or in the wall of a body cavity. The prior art method of placing the submucosal or extracellular matrix-derived tissue is described in U.S. Pat. No. 6,790,220, which is herein incorporated by reference, a simplified version of which is reproduced in FIGS. 1A-1D.

An introducer 10 with a sheath 11 carrying a ribbon or sheet 12 of extracellular matrix-derived tissue is inserted through the skin, the underlying muscle tissue, and through the blood vessel wall. Ribbon or sheet 12 includes a cuff 14 and an extended length 15. The cuff 14 is usually situated and secured directly above a hole 13 in the sheath 11, in which the extended length 15 is inserted. The outer diameter of the cuff 14 is greater than the outer diameter of the sheath 11. As is also shown in FIG. 1A, pull-up tether 16 is woven through the extended length 15 and pull down tether 18 is woven into the cuff 14 and both tethers are exposed externally. The introducer 10 is inserted until the greater diameter of the cuff 14 prevents further insertion of the introducer 10. The cuff 14 is then released so that it is free to move relative to the sheath 11. The sheath 11, is advanced as the cuff remains in position and the extended length is withdrawn from the interior of the sheath 11 through the hole 13.

When the procedure is completed, the entry to the artery will need to be closed. As shown in FIGS. 1B-1D, the user pulls the tethers 16, 18 to bunch the ribbon or sheet 12 into a ball 15. When the sheath remains inserted, the ball 15 is held to the side of the puncture site by the sheath 11. When the sheath is removed, the ball 15 moves into the puncture site, sealing the puncture site immediately. When the user determines that the patch completely seals the hole in the tubular structure, the tethers 16, 18 may then be cut and removed.

This method of sealing a hole in a tubular structure has an excellent safety profile, but can suffer from inconsistent tether compression of the device. If the user pulls too hard on the tether, the ribbon or sheet may be pulled out of position to seal the hole. At the same time, if the user does not pull hard enough on the tether, the ribbon or sheet will not be compressed sufficiently to effectively seal the hole. Even after the ribbon or sheet is compressed into a ball, by removing the sheath a space is created within the cuff. An incomplete mechanical closure of the hole may contribute to longer hold times being necessary to reach hemostasis. Some users advocate adding a "little" pull on the suture tether to further tighten the ball after removing the sheath, but it's success is very operator dependent and inconsistent.

In addition, in order to determine when hemostasis has been achieved, the user must hold pressure externally on the skin over the puncture site and intermittently check for bleeding at the skin level. However, this method is not consistent in revealing what is actually going on at the arteriotomy site, sometimes very deep inside other tissue. This uncertainty can lead to hold times that are longer or shorter than needed contributing to hematomas or ecchymosis.

Accordingly, there is a need for surgical techniques suitable for sealing punctures in a tubular tissue structure or in the punctured wall of a body cavity, such as a heart chamber, or a body cavity of another organ, that is more consistent between users and allows more certainty in determining hemostasis.

BRIEF SUMMARY

The present invention provides among other things an apparatus and method for sealing punctured tubular tissue structures, including arteries and veins, such as punctures which occur during diagnostic and interventional vascular and peripheral catheterizations, or for sealing a puncture in the wall of a body cavity. More specifically, the apparatus and method of the present invention employ a stabilizer to allow more consistent sealing of punctures in tubular tissue structures, such as blood vessels, or in the wall of a body cavity.

It is an object of the invention to provide a method and apparatus for sealing a hole in a tubular tissue structure or in the wall of a body cavity.

It is another object of the invention to provide an accessory stabilizer that may be used with existing devices used to seal a hole in a tubular tissue structure or in the wall of a body cavity.

The above and other objects are achieved using a device involving an introducer element with a sheath, a stabilizer, and a ribbon or sheet of material having an extended portion and a cuff detachably coupled to the sheath. A tether is connected to the ribbon or sheet of material to manipulate the shape or position of the material. In a particular embodiment, the stabilizer is positioned about the sheath above the cuff, at a distance substantially equal to the length of the extended portion of the ribbon or sheet of material. This allows the sheath to be inserted the distance of the extended portion of the ribbon or sheet fully exposing the ribbon or sheet from the interior of the sheath before the cuff contacts the stabilizer.

The stabilizer may be a length of hollow tubing that is detachably coupled to the sheath. The tether may pass between the sheath and the stabilizer. The stabilizer may further comprise a valve to selectively allow blood or other materials through the stabilizer. The stabilizer may alternatively be a ring integral to the sheath of greater circumference than the portion of the sheath below the ring. In a particular embodiment, the stabilizer is detachably coupled to the sheath such that tension on the tether detaches the stabilizer from the sheath.

The sheath may be marked to indicate a distance from the end of the sheath to the mark substantially equal to the length of the stabilizer. In this way, the mark will appear above the stabilizer when the sheath has been removed from the puncture site.

In another embodiment of the invention, a stabilizer is provided involving a hollow tube that is detachably coupled to an existing apparatus for sealing a puncture site in a tubular structure.

The above and other objects may also be achieved using a method involving inserting an introducer with a sheath into the puncture site in the tubular structure. A ribbon or sheet of material and a stabilizer are coupled to the sheath, and a tether is coupled to the ribbon or sheet of material to allow manipulation of the ribbon or sheet of material. The ribbon or sheet of material has a cuff and an extended portion, the cuff being situated around the exterior circumference of the sheath and the extended portion initially residing inside the sheath entering through a hole in the sheath adjacent to where the cuff is coupled to the extended portion of the ribbon or sheet. The sheath is entered into the tubular structure until the wider cuff makes entry into the puncture site more difficult. In a particular embodiment, the cuff and the and stabilizer are removably coupled to the sheath to restrict movement of the ribbon or sheet and stabilizer during insertion. When the cuff contacts the puncture site, the cuff is detached from the sheath to allow movement of the ribbon or sheet relative to the sheath and the stabilizer may be de-coupled from the sheath and contacted to the cuff to stabilize the cuff against the puncture site. The sheath is then further inserted into the tubular structure to expose the extended length from the sheath. The stabilizer maintains contact with the cuff as the ribbon or sheet is manipulated into a ball position to seal the puncture site upon removal of the sheath.

Once the ribbon or sheet is pulled into a compact ball, the tether may be locked in position. The sheath may be withdrawn, while the stabilizer remains in contact with the cuff to secure the cuff in position about the puncture site. The sheath may have a mark indicating to the user when the sheath has been removed from the puncture site. When the sheath is removed, the balled ribbon or sheet is pulled into the puncture site, sealing the tubular structure. In a particular embodiment, the stabilizer is a hollow tube and the user may hold the stabilizer in contact with the cuff and the puncture cite to ensure that bleeding has stopped at the puncture cite. This is particularly helpful when the puncture site is not visible within the body of a patient. If any bleeding is observed, the ribbon or sheet may be further manipulated with the tether to more completely seal the puncture site until a lack of bleeding at the puncture site is observed through the stabilizer. If desired, a thrombogenic material may be introduced to the puncture site through the stabilizer.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. Absent a clear statement of intent to apply a "special" definition to a term, it is the inventors' intent and desire that the simple, plain and ordinary meaning to the terms be applied to the interpretation of the specification and claims.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

In one application of the invention, the present invention is related to an apparatus and a method for sealing a puncture in a tubular tissue structure, such as a blood vessel, or in the wall of a body cavity. The apparatus and method of the present invention can be used to seal a puncture in a tubular tissue structure, such as a blood vessel, or in the wall of a body cavity, that has been created intentionally or unintentionally during a surgical procedure or nonsurgically (e.g., during an accident). Punctures made intentionally include vascular punctures made in various types of vascular, endoscopic, or orthopaedic surgical procedures, or punctures made in any other type of surgical procedure, in coronary and in peripheral arteries and veins or in the wall of a body cavity. Such procedures include angiographic examination, angioplasty, laser angioplasty, valvuloplasty, atherectomy, stent deployment, rotablator treatment, aortic prosthesis implantation, intraortic balloon pump treatment, pacemaker implantation, any intracardiac procedure, electrophysiological procedures, interventional radiology, and various other diagnostic, prophylactic, and therapeutic procedures such as dialysis and procedures relating to percutaneous extracorporeal circulation.

Figure 1A:
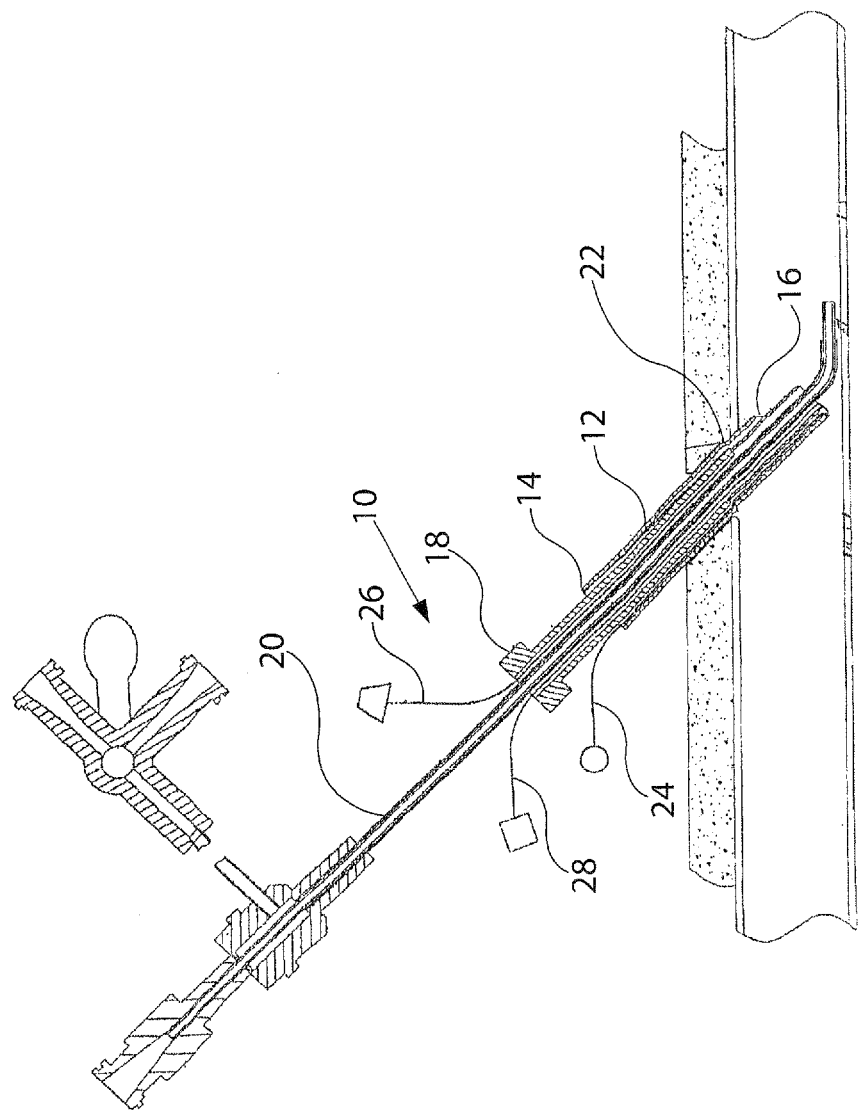
FIGS. 1A-D illustrate a prior art method and introducer elements for use in sealing access to a tubular tissue structure or a body cavity.
Figure 1B:
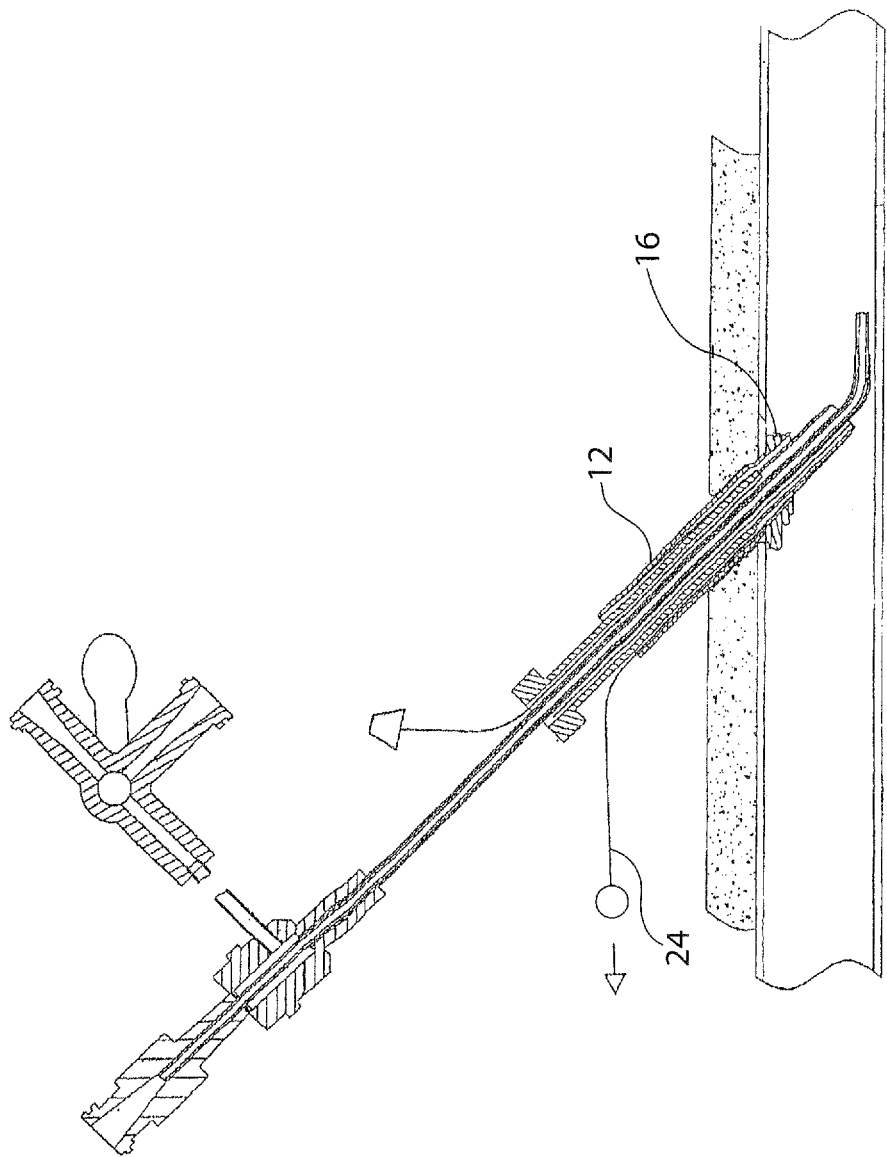
Figure 1C:
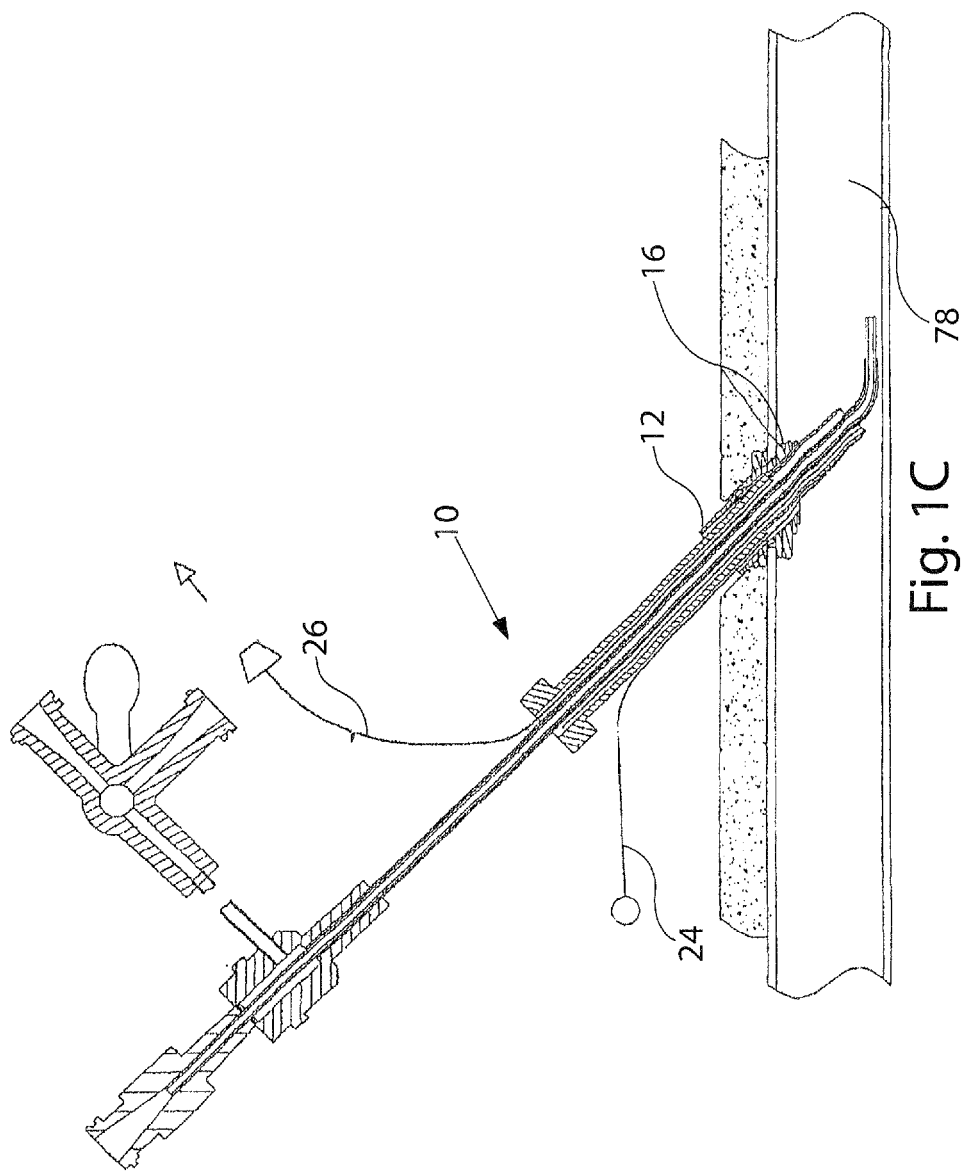
Figure 1D:
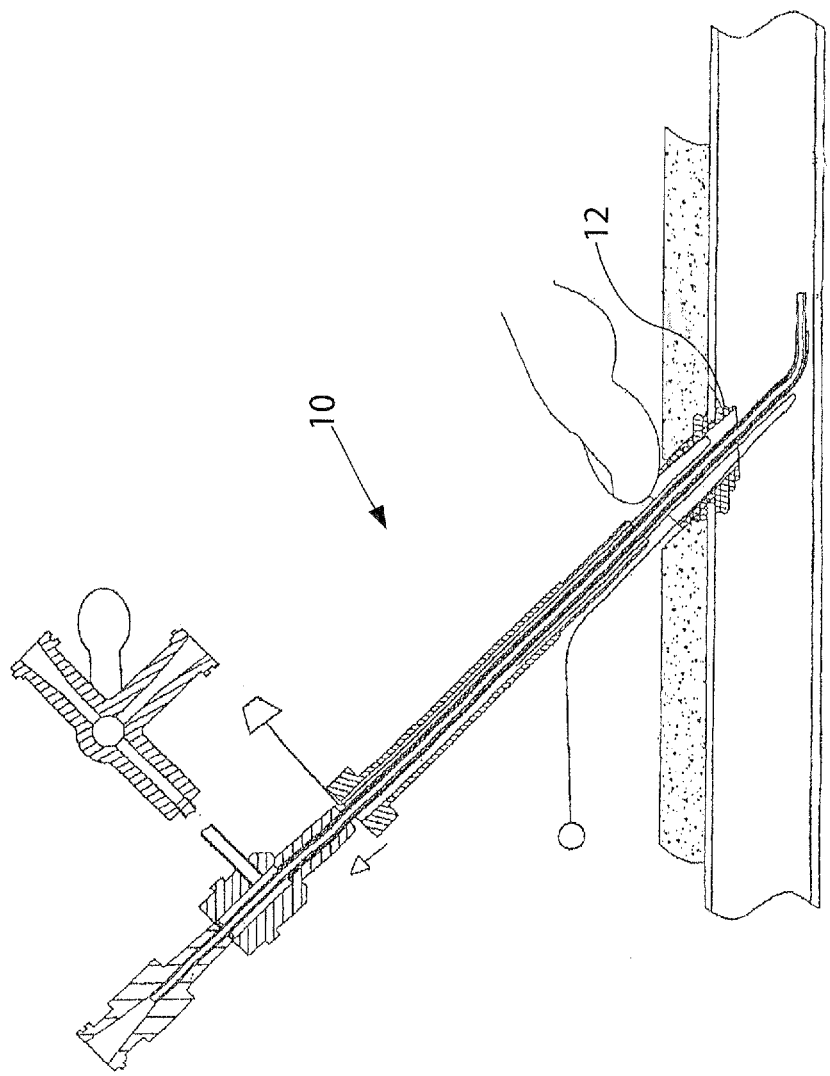
Figure 2:
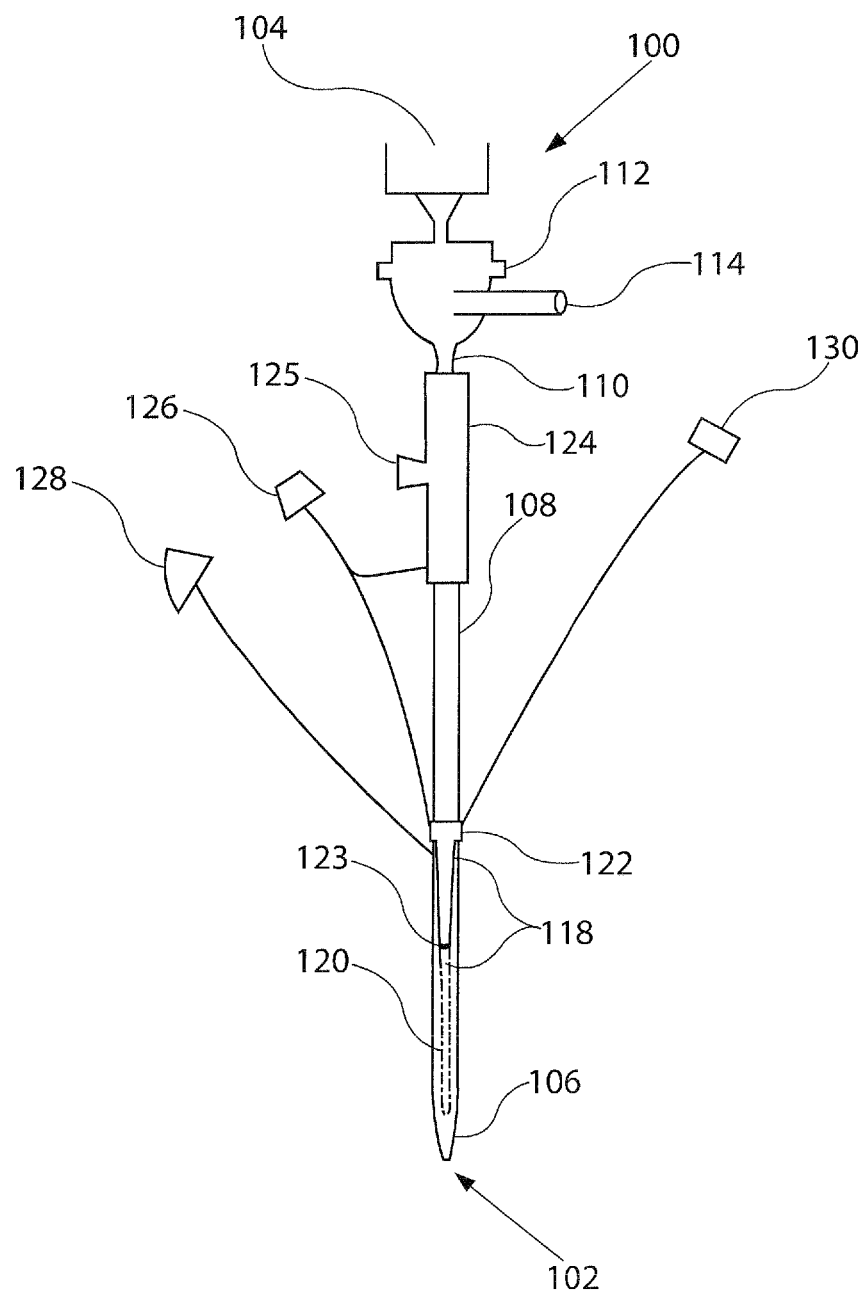
FIG. 2 depicts the introducer apparatus of the present invention.

Referring now to the drawings, FIG. 2 illustrates an introducer 100 adapted for catheterization, exemplary of the type of introducer element that may be used in accordance with the present invention. Although an introducer 100 adapted for use in catheterization procedures is illustrated in FIG. 2, it is understood that the present invention is applicable to any type of introducer element used to provide access to the lumen of a tubular tissue structure, such as a blood vessel, or to a body cavity. For example, the present invention is applicable to an introducer element such as a needle, a cannula, a guide wire, an introducer element adapted for dialysis, a trocar, or any other introducer element used to access the lumen of a tubular tissue structure or a body cavity.

An introducer 100 as depicted in FIG. 2 can be used when performing catheterization procedures in coronary and peripheral arteries and veins. Typically, a catheter is introduced into the vascular system by first penetrating the skin, underlying muscle tissue, and the blood vessel with a needle, and a guide wire is inserted through the lumen of the needle and enters the blood vessel. Subsequently, the needle is stripped off the guide wire and an introducer 100 is fed over the guide wire and pushed through the skin and through the vessel wall to enter the vessel. The guide wire can then be removed and a catheter is fed through the lumen of the introducer 100 and advanced through the vascular system until the working end of the catheter is positioned at a predetermined location. Alternatively, the guide wire may be left in place throughout the procedure and the introducer 100 removed before the guide wire is removed. At the end of the catheterization procedure, the catheter is withdrawn. The introducer 100 is also removed and the opening through which, for example, the introducer 100 is inserted must be sealed as quickly as possible once the procedure is completed. Although a typical catheterization procedure utilizing an introducer 100 is described, the described procedure is non-limiting. Furthermore any embodiment of the introducer 100 described below is applicable to any other introducer element for use in accessing the lumen of a tubular tissue structure or a body cavity in accordance with the invention.

The present invention may be employed, for example, to rapidly seal a puncture site in a blood vessel upon completion of a catheterization procedure. The introducer 100 illustrated in FIG. 2 is an exemplary embodiment and has a user distal end 102 for insertion into a blood vessel and a user proximal end 104. A standard introducer comprises a dilator 106 and a sheath 108 which extends axially over the dilator 106, a sheath cap 110 disposed axially over a portion of the sheath 108 and a valve cap 112 connected to the sheath cap 110 and to a side port tube 114. Sheath 108 may be extended to accommodate particularly obese patients. A standard introducer may also comprise a three-way valve (not shown) and a syringe connector (not shown) connected to an end of the side port tube 114, adapted for the attachment of a syringe to the introducer 100 and connected to the valve cap 112. The introducer 100 depicted in FIG. 2 further comprises a stabilizer and a ribbon or sheet 118, that may be composed of submucosal tissue or another extracellular matrix-derived tissue.

The ribbon or sheet 118 has an extended portion 120 which is inserted into a tubular tissue structure, such as a blood vessel, and a cuff 122 which remains outside of the punctured vessel wall. The cuff 122 extends about the circumference of the sheath 108 and the extended portion enters into a hole 123 in the sheath 108, and extends axially toward the distal end 102 of the sheath.

A stabilizer 124 is placed about the sheath 108 between the ribbon or sheet 118 and the sheath cap 110. Stabilizer 124 may included a knob, handle, or ergonomic protrusion 125 for the user's convenience in manipulating the stabilizer 124. The stabilizer may extend axially from the sheath cap 110 to the cuff 122. Preferably, the stabilizer 124 is separated from the ribbon or sheet 118 by a distance approximately equal to the axial length of the ribbon or sheet 118 and is detachably coupled to the sheath 108 such that the stabilizer 124 is initially immobile, but may be detached so that it is free to move in an axial direction relative to the sheath 108. The distance that the stabilizer is separated from the ribbon or sheet 118 allows the sheath 108 with the attached stabilizer 124 to move relative to the ribbon or sheet 118 such that the extended portion 120 is withdrawn from the hole 123 as the introducer 100 is inserted into the puncture site.

The cuff 122 of the ribbon or sheet 118 may initially be held in place, for example, by a wire attached to the cuff 122 of the ribbon or sheet 118 and the body of the sheath 108, the sheath cap 110 or the valve cap 112. As a result, the ribbon or sheet 118 is prevented from being pushed up or down relative to the sheath 108 of the introducer 100 when the user inserts the introducer 100 through, for example, a vessel wall with his hand in contact with the ribbon or sheet 118. The wire may be coupled to the release tether 126, described below, or may be cut to allow the cuff 122 of the ribbon or sheet 118 to move axially relative to the sheath 108 and to be gathered externally to seal the puncture site. In other embodiments, the cuff 122 of the ribbon or sheet 118 or other parts of the ribbon or sheet 118 may be held in place by metal or plastic clamps, O-rings, or the like, which may be removed from the end of the ribbon or sheet 118 when it is necessary to gather the ribbon or sheet 118 externally to seal the puncture site.

Figure 3A:
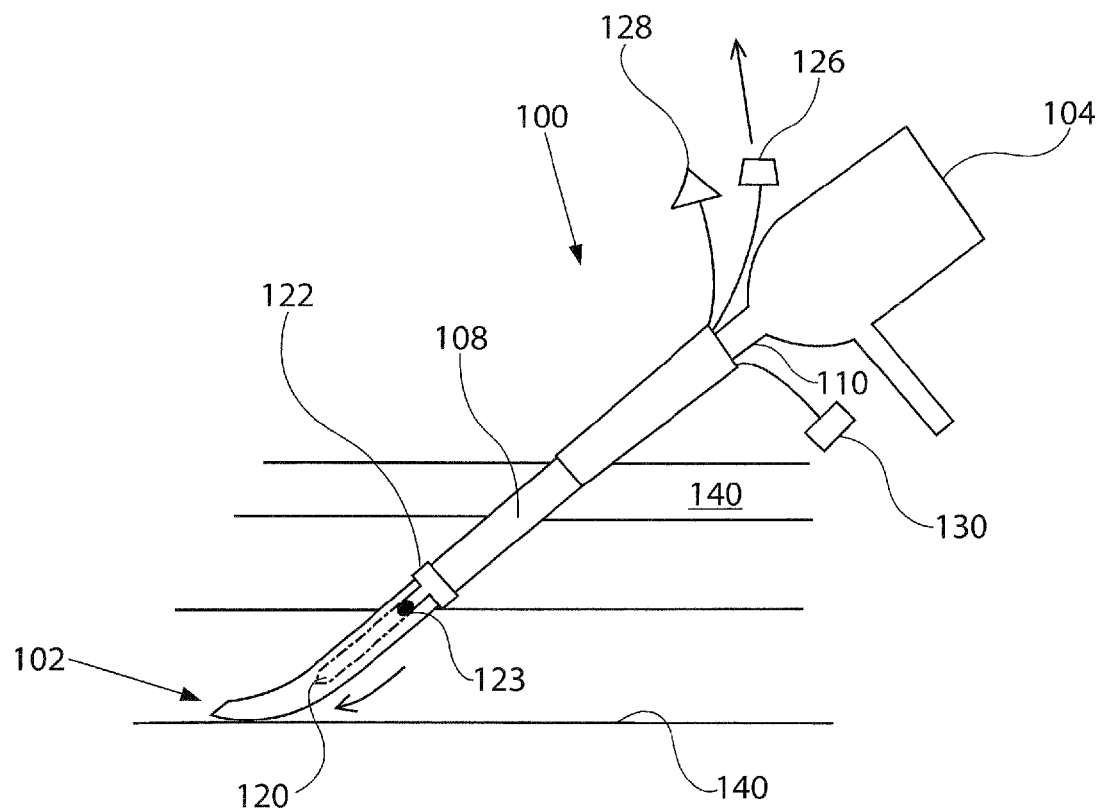
FIGS. 3A-E illustrate the method and elements of the invention for use in sealing a tubular tissue structure or a body cavity.

As also depicted in FIG. 2 and FIG. 3A, in one embodiment the extended portion 120 of the ribbon or sheet 118 is initially situated inside the sheath 108 to prevent the ribbon or sheet 118 from rolling up the introducer 100 upon insertion into the blood vessel when the ribbon or sheet 118 is positioned during insertion into a blood vessel 140. Although the ribbon or sheet 118 is depicted inside the sheath 108 in FIG. 2, any configuration of the extended portion 120 of the ribbon or sheet 118 can be used which prevents the ribbon or sheet 118 from rolling up the introducer 100 upon insertion into the blood vessel.

The ribbon or sheet 118 may have one or more tethers 126, 128 attached at or near to the cuff 122 of the ribbon or sheet 118 and a tether 130 attached at or near to the extended portion 120 of the ribbon or sheet 118. For example, one or more pull-up tethers 130 may be attached at or near to the extended portion 120 of the ribbon or sheet 118, and one or more pull-down tethers 128 may be attached at or near to the cuff 122 of the ribbon or sheet 118. One or more release tethers 126 may be attached at or near to the cuff 122 of the ribbon or sheet 118, and to the stabilizer 124. The function of the various types of tethers is described below.

The pull-up tether 130 is attached to the ribbon or sheet 118 at or near the extended portion 120 of the ribbon or sheet 118 and is woven axially upwards towards the cuff 122 of the ribbon or sheet 118 (and thus upwards towards the puncture site). Thus, a portion of the pull-up tether is inserted into the blood vessel 140 when the introducer 100 is pushed through the blood vessel wall and a portion of the pull-up tether 130 remains externally exposed to be manipulated by a user. Upon completion of the procedure, such as catheterization, the portion of the pull-up tether 130 remaining externally exposed is pulled to gather the extended portion 120 of the ribbon or sheet 118 into a compressed ball shape 127 adjacent to the puncture site as shown in FIG. 3.

The pull-down tether 128 is attached at or near the cuff 122 of the ribbon or sheet 118 and extends axially downwards between the ribbon or sheet 118 and the positioning tube 116 towards the distal end of the positioning tube 116. The pull-down tether 128 further extends radially inwards under the positioning tube 116 and then extends axially upwards towards the proximal end of the positioning tube 116. Thus, the attached end and the unattached end of the pull-down tether 128 remain externally exposed when the introducer 100 is inserted into the blood vessel wall. Upon completion of the procedure the unattached end of the pull-down tether 128 is pulled to gather the cuff 122 of the ribbon or sheet 118 into a compressed ball shape 129 at the puncture site from the outside of the vessel wall as shown in FIG. 4.

In one embodiment of the invention, a release tether 126 is attached to the ribbon or sheet 118. The distal end of the release tether 126 is attached at or near the cuff 122 of the ribbon or sheet 118. The release tether 126 extends axially upwards towards the proximal end of the sheath 108. The proximal end of the release tether 126 remains externally exposed. The release tether is pulled to allow the ribbon or sheet 118 to move relative to the sheath 108. The release tether 126 may also be coupled to the stabilizer 124, such that a single tether releases the ribbon or sheet 118 and the stabilizer 124 to move relative to the sheath 108.

Preferably the present invention has one or more release tethers 126, one or more pull-up tethers 128, and one or more pull-down tethers 128. However, the invention may have any combination of pull-up tethers 130, pull-down tethers 128, and release tethers 126, or may lack one or more types of tethers. For example, the invention may lack a release tether 126 or a pull-down tether 128.

Tethers with different functions (i.e., the release tether 126, the pull-up tether 130, and the pull-down tether 128) may have different indicia disposed thereon, such as different colors, so that the user can easily identify the tether with the desired function. Alternatively, tethers with different functions may have different caps attached to the externally exposed ends so that the tether with the desired function can be easily identified. The tethers are preferably made of resorbable thread and the tethers can be attached to the ribbon or sheet 118 by any suitable means. For example, the tethers can be tied to the ribbon or sheet 118 or hooked to the ribbon or sheet 118 by using hooks, barbs, etc. (e.g., for tethers with attachment points that remain externally exposed when the introducer 100 is inserted into the vessel wall).

The present invention is also directed to a method of sealing a puncture site in the wall of a tubular tissue structure or the wall of a body cavity. Referring to FIG. 3A, the method comprises the steps of inserting an introducer 100 into the puncture site through the skin 142 with a stabilizer and a ribbon or sheet 118 having a cuff 122 and an extended portion 120. The cuff 122 of the ribbon or sheet 118 remains outside of the punctured wall and the extended portion 120 of the ribbon or sheet 118 is inserted into the tubular tissue structure. Once the extended portion 120 of the ribbon or sheet 118 has been inserted, the ribbon or sheet 118 and the stabilizer 124 is released to move axially relative to the sheath 108 by pulling the release tether 126. The stabilizer 124 contacts the cuff 122 and holds the ribbon or sheet 118 in position while the sheath 108 may be further inserted into the tubular tissue structure to expose the extended portion 120 of the ribbon or sheet 118.

Figure 3B:
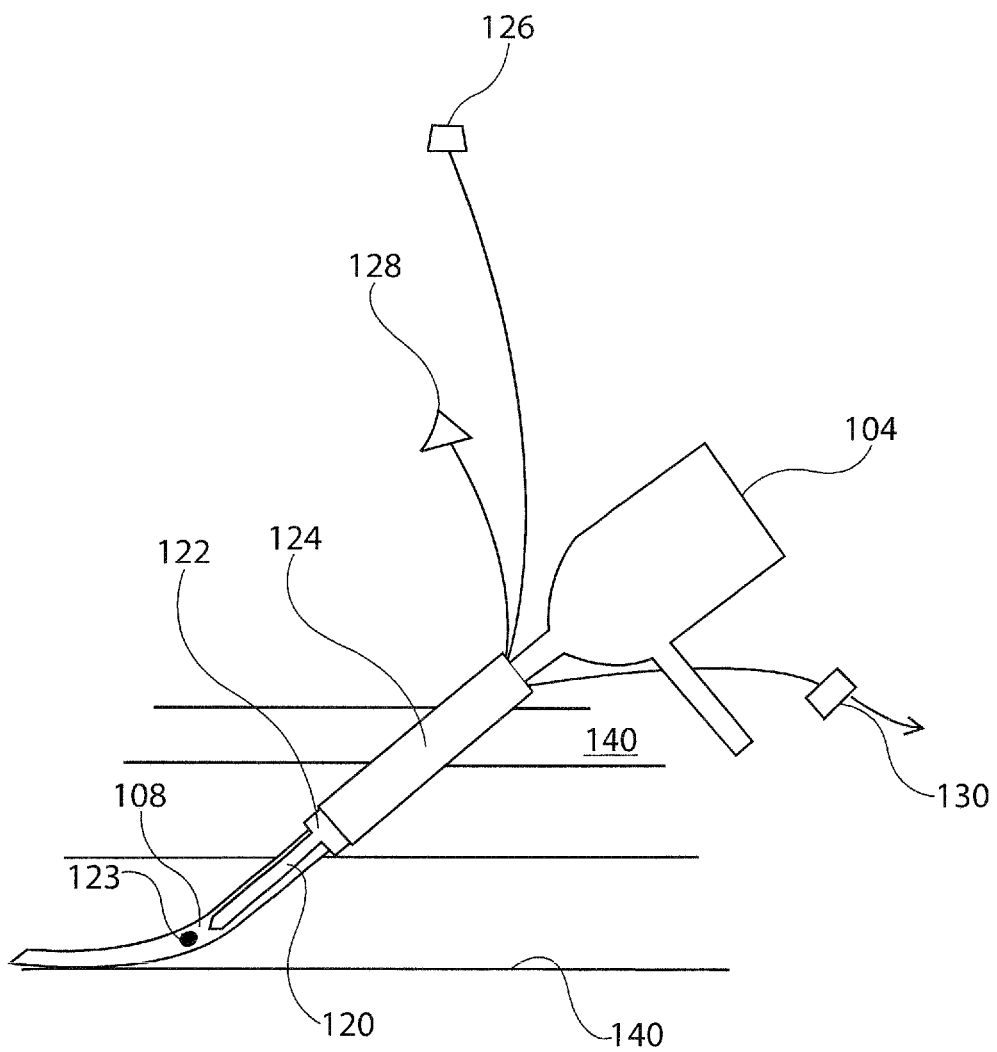
Figure 3C:
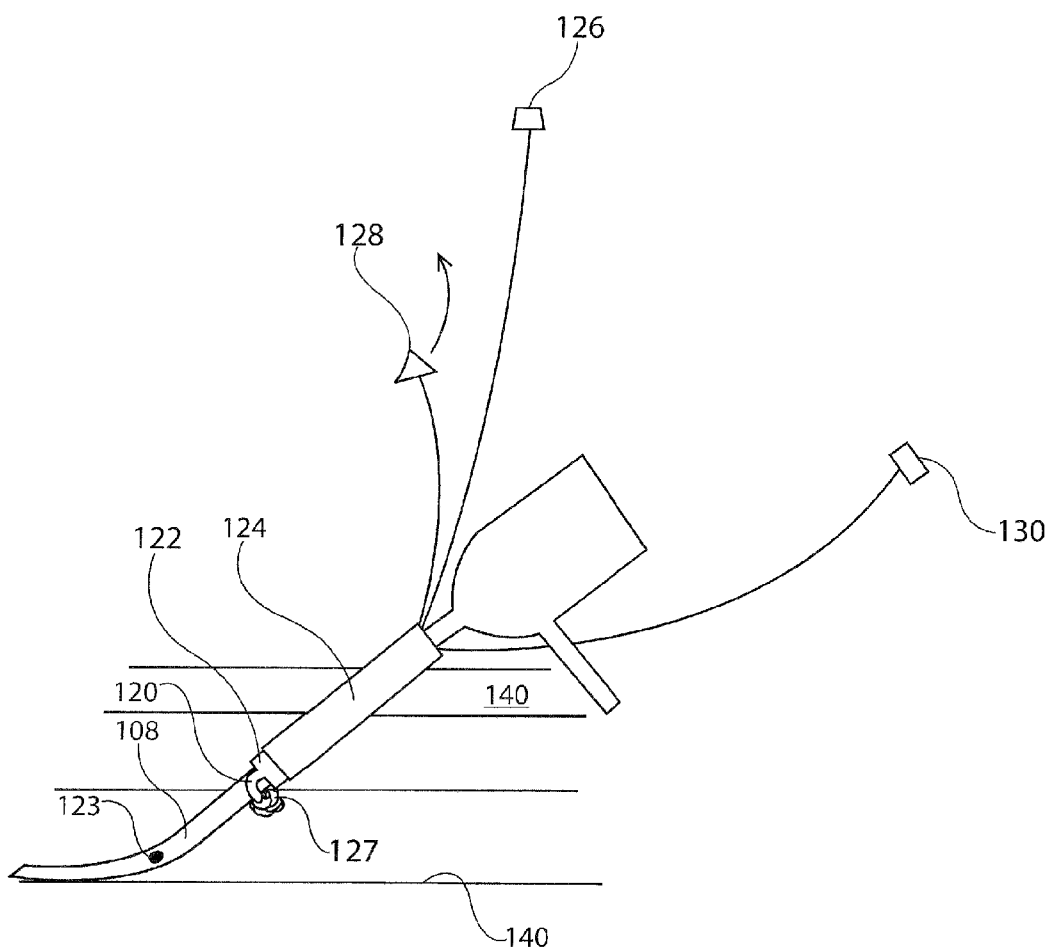

Referring to FIGS. 3B-C, the sheath may be inserted until the stabilizer 124 abuts the cap 110. Tethers 128, 130 may be pulled to compress the cuff 122 and extended portion, 120 respectively, of the ribbon or sheet 118 about the puncture site while stabilizing the cuff 122 of the ribbon or sheet 118 in position relative to the puncture site with the stabilizer 124. The user pulls the user proximal end of the pull-up tether 130 to gather the extended portion 120 into a ball shape 127 proximal to the puncture site in the blood vessel wall. The user proximal end of the pull-down tether 128 is also pulled to position the cuff 122 in a ball shape 129 proximal to the exterior of the puncture site as shown in FIGS. 3C-D.

Figure 3D:
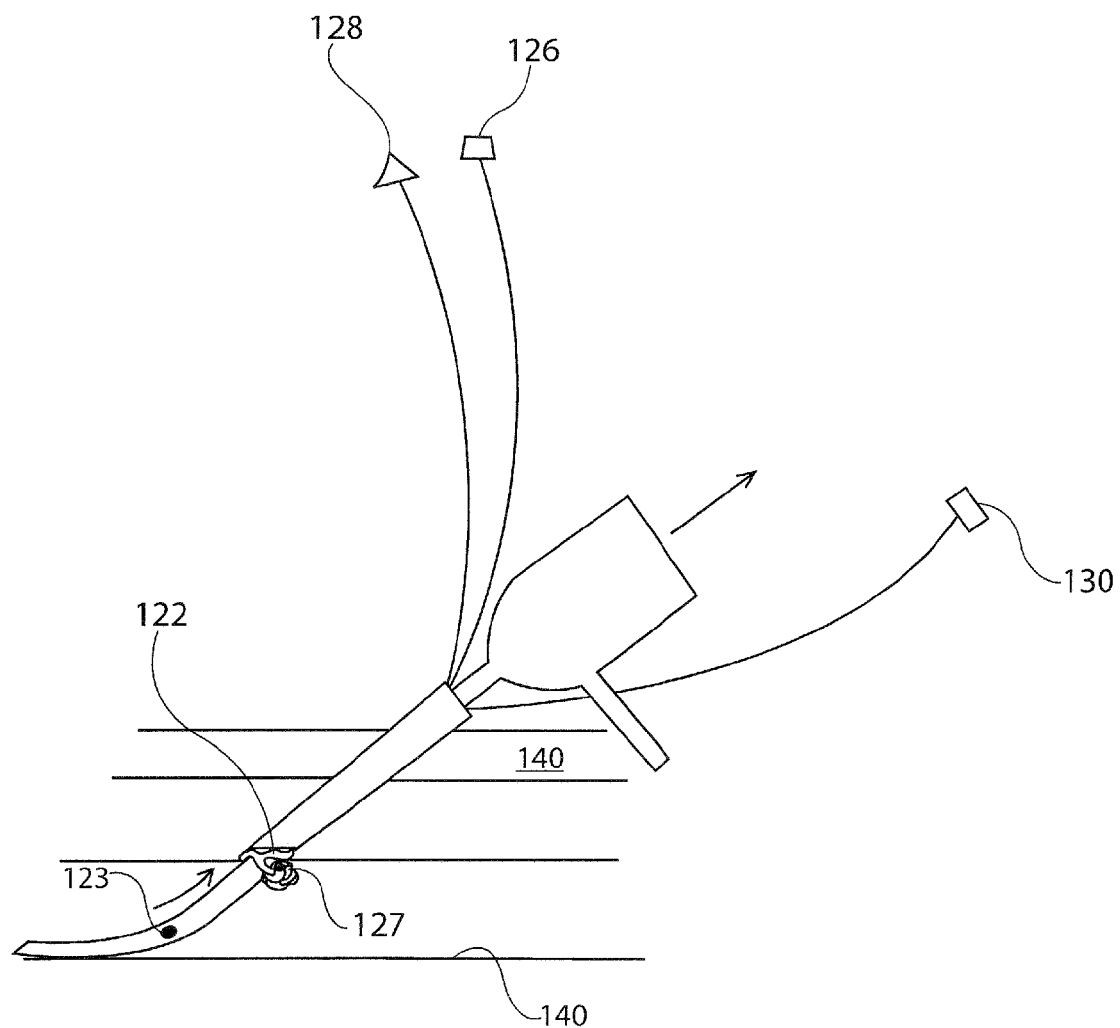
Figure 3E:
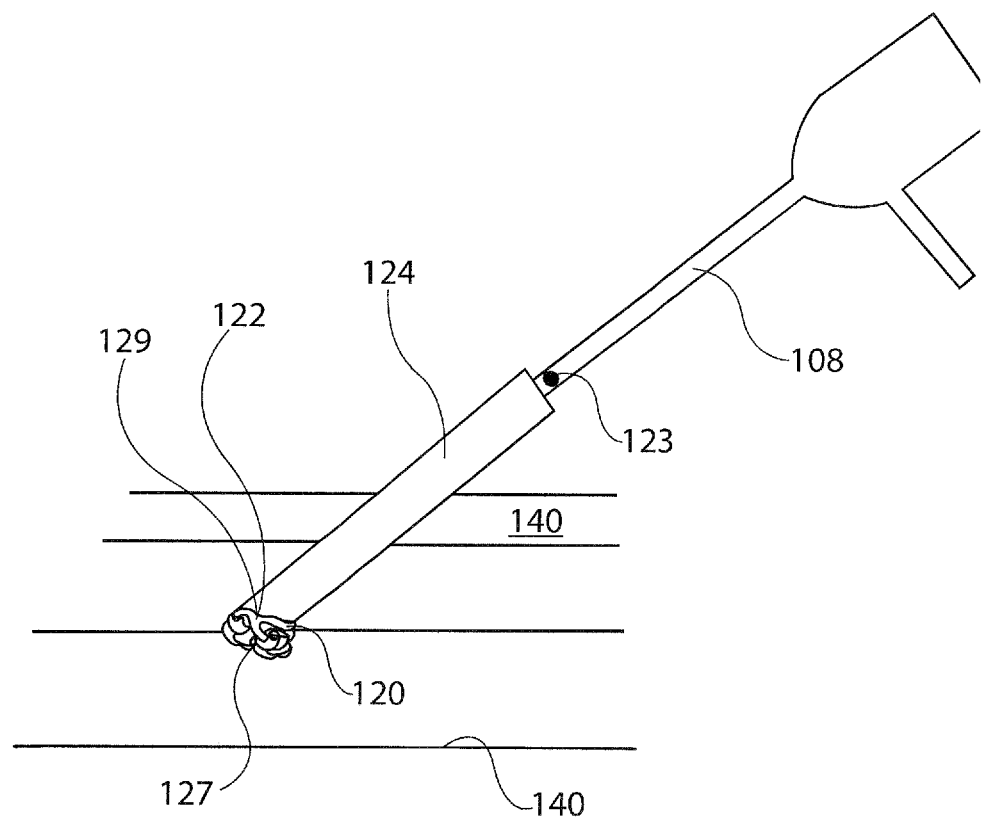
Figure 3E:
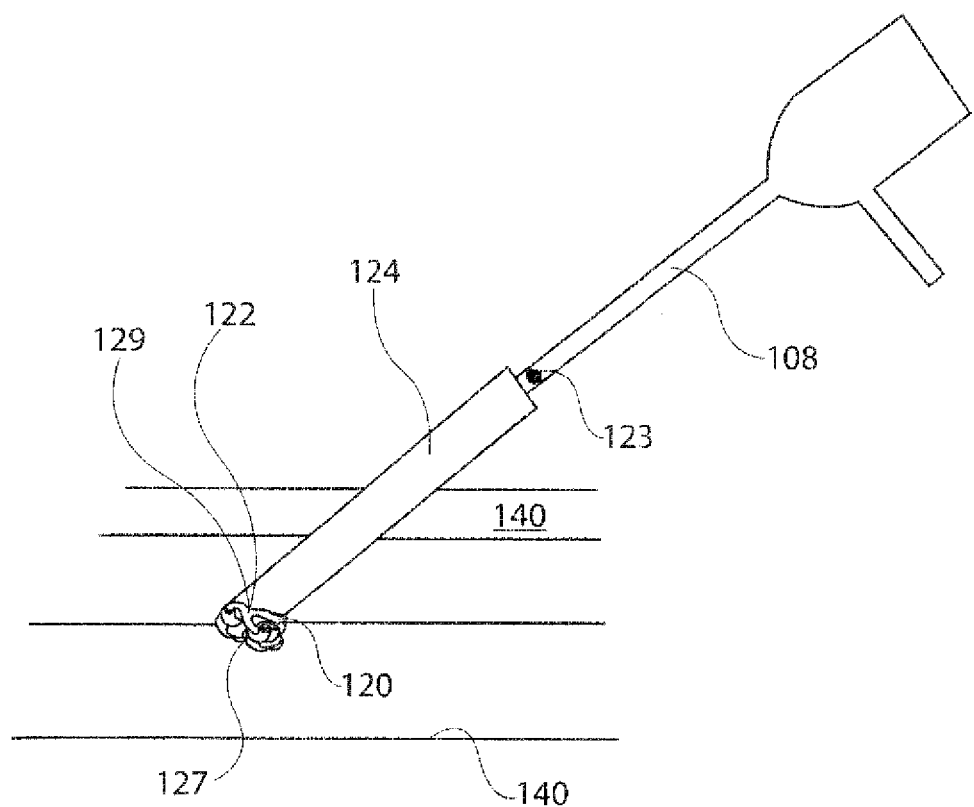

Referring to FIGS. 3D-E, as the sheath 108 is pulled out of the puncture site, the cuff 122 of the ribbon or sheet 118 can be held in place by the stabilizer 124. Mark 140 on the sheath 108 indicates that the distal end 102 of the sheath 108 has cleared the puncture site. The compressed balls 127, 129 of the ribbon or sheet 118 replace the sheath 108 in the puncture site to form a hemostatic seal in the puncture site. If some bleeding at the puncture site remains and is detected after the sheath 108 is removed, the tethers 130, 128 may be further tensioned while the stabilizer 124 holds the ribbon or sheet 118 in position to more tightly compress and more effectively position the ribbon or sheet 118 to effectively seal the puncture site. In a closed procedure, the stabilizer 124 couples the puncture site to the exterior of the patient's skin, and the user may visually confirm hemostasis at the artery by observing whether blood is expelled from the stabilizer 124. If bleeding persists, the user may exert more tension on the tethers as described above. In some embodiments, the stabilizer 124 includes a valve 125 to prevent blood from being expelled from the stabilizer.

The exposed portion of the tethers can be removed by cutting. In the above-described method, the ribbon or sheet 118 can be gathered into the puncture site after, during, or before removal of any of the components of the introducer element.

In one embodiment of the invention a puncture site is sealed in the wall of a blood vessel 140 in a patient undergoing catheterization. Although the use of an introducer 100 adapted for catheterization is illustrated in FIGS. 2-3, it is understood that the present invention is applicable to any type of procedure in which an introducer element is used to provide access to the lumen of a tubular tissue structure, such as a blood vessel, or to a body cavity. For example, the present invention is applicable to procedures in which an introducer element such as a needle, a cannula, a guide wire, an introducer element adapted for dialysis, a trocar, or any other introducer element used to access the lumen of a tubular tissue structure or to a body cavity is used.

I claim:

1. A method of sealing a puncture site in the wall of a tubular tissue structure or in the wall of a body cavity, said method comprising the steps of:

inserting an introducer into the puncture site, the introducer having a sheath, a sheath cap, a stabilizer detachably coupled to the sheath, wherein the stabilizer, upon detachment from the sheath is free to move in an axial direction relative to the sheath, and a ribbon or sheet of material, wherein the ribbon or sheet of material has at least one tether, an extended portion and a cuff, wherein the cuff of the ribbon or sheet remains outside of the punctured wall and the extended portion of the ribbon or sheet is positioned in the lumen of the tubular tissue structure or the body cavity;

detaching the stabilizer from the sheath, and axially moving the stabilizer relative to the sheath to contact the cuff and to stabilize the cuff relative to the puncture site; and positioning the ribbon or sheet to substantially seal the puncture site while the stabilizer is in contact with the cuff.

2. The method of claim 1, further comprising the step of withdrawing the sheath from the puncture site while the stabilizer substantially remains in contact with the cuff.

3. The method of claim 2, wherein the stabilizer comprises a hollow tube and further comprising the step of monitoring the stabilizer for evidence of bleeding at the puncture site.

4. The method of claim 3, wherein the puncture site is in a body and the stabilizer extrudes from the body in which the puncture site is located.

5. The method of claim 4, further comprising the step of adjusting the position of the ribbon or sheet if evidence of bleeding is observed.

6. The method of claim 3, further comprising the step of introducing a thrombogenic material to the puncture site through the stabilizer.

7. The method of claim 1, further comprising the step of releasing the ribbon or sheet from a fixed position relative to the ribbon or sheath.

8. The method of claim 7, further comprising the step of inserting the sheath farther into the puncture site after the ribbon or sheet is released from a fixed position relative to the sheath to help position the ribbon or sheath.

9. The method of claim 1, further comprising the steps of applying tension to the tether to position the ribbon or sheet to substantially seal the puncture site; and locking the tether to secure the position of the ribbon or sheet in the puncture site.

10. An apparatus for sealing a puncture site in the wall of a tubular tissue structure or the wall of a body cavity in a patient, the apparatus comprising:

an introducer element having a sheath;

a sheath cap;

a ribbon or sheet of material having an extended portion and a cuff, wherein the ribbon or sheet of material is detachably coupled to the sheath;

a tether coupled to the ribbon or sheet of material to manipulate the shape or position of the material; and a stabilizer detachably coupled to the sheath, wherein the stabilizer, upon detachment from the sheath, is free to move in an axial direction relative to the sheath whereby to contact and stabilize the cuff relative to the puncture site.

11. The apparatus of claim 10, wherein the extended portion of the ribbon or sheet of material has a length, and wherein the stabilizer is positioned about the sheath at a distance from the cuff of the ribbon or sheet of material substantially equal to a length of the extended portion of the ribbon or sheet of material.

12. The apparatus of claim 10, wherein the stabilizer is a length of hollow tubing.

13. The apparatus of claim 12, wherein the stabilizer includes a valve.

14. The apparatus of claim 10, wherein the tether passes between the sheath and the stabilizer.

15. The apparatus of claim 10, wherein the stabilizer is integral to the sheath.

16. The apparatus of claim 10, wherein the ribbon or sheet of material is a ribbon or sheet of submucosal tissue or another extracellular matrix-derived tissue.

17. The apparatus of claim 10, wherein the stabilizer is coupled to the sheath such that manipulation of the tether detaches the stabilizer from the sheath.

18. The apparatus of claim 10, wherein the stabilizer has a length, and wherein the sheath has an end and a mark indicating a distance from the end to the mark substantially equal to the length of the stabilizer.

19. The apparatus of claim 10, wherein the stabilizer has a projection to allow a user to manipulate the stabilizer.

* * * * *

UNITED STATES PATENT AND TRADEMARK OFFICE
CERTIFICATE OF CORRECTION

PATENT NO. : 8,998,950 B2
APPLICATION NO. : 13/405911
DATED : April 7, 2015
INVENTOR(S) : Berens It is certified that error appears in the above-identified patent and that said Letters Patent is hereby corrected as shown below:

Delete fig. 3E and substitute therefor the drawing sheet, consisting of fig. 3E as shown on the attached page.

Signed and Sealed this
Fifth Day of January, 2016

Michelle K. Lee
*Director of the United States Patent and Trademark Office*